United States Patent [19]

Rich et al.

[11] Patent Number: 4,657,028
[45] Date of Patent: Apr. 14, 1987

[54] BLOOD SAMPLING DEVICE

[75] Inventors: Russell Rich, North Ridgeville, Ohio; Joergen Andersen, Herlev, Denmark

[73] Assignee: Radiometer A/S, Copenhagen, Denmark

[21] Appl. No.: 724,801

[22] Filed: Apr. 19, 1985

Related U.S. Application Data

[63] Continuation of Ser. No. 477,972, Mar. 23, 1983, abandoned.

[30] Foreign Application Priority Data

Feb. 21, 1983 [DK] Denmark ................ 729/83

[51] Int. Cl.⁴ .............................................. A61B 5/00
[52] U.S. Cl. ................................. 128/765; 128/763; 604/246
[58] Field of Search ............... 128/763, 764, 765, 766; 604/236, 237, 243, 246, 247, 249; 73/864.01, 863.01, 863.23

[56] References Cited

U.S. PATENT DOCUMENTS 3,028,862  4/1962  Prater, Jr. .
3,063,451 11/1962  Kowalk .
3,330,282  7/1967  Visser et al. .
3,464,412  9/1969  Schwartz .
3,596,652  8/1971  Winkelman .
3,785,367  1/1974  Fortin et al. .
3,809,298  5/1974  Harris, Sr. et al. .
3,848,581 11/1974  Cinqualbre et al. .
3,908,638  9/1975  Porcher et al. .
3,930,492  1/1976  Hatsuno et al. .
3,943,917  3/1976  Johansen .
3,960,139  6/1976  Bailey .
3,978,846  9/1976  Bailey .
4,004,587  1/1977  Jess .
4,073,288  2/1978  Chapman .
4,133,304  1/1979  Bailey .
4,172,448 10/1979  Brush .
4,173,222 11/1979  Muetterties .
4,206,768  6/1980  Bailey .
4,257,426  3/1981  Bailey .
4,266,558  5/1981  Akhavi .
4,266,559  5/1981  Akhavi .
4,299,238 11/1981  Baidwan et al. .
4,326,540  4/1982  Bailey et al. .
4,340,067  7/1982  Rattenborg .
4,361,155 11/1982  Anastasio .
4,373,535  2/1983  Martell .
4,572,210  2/1986  McKinnon .

FOREIGN PATENT DOCUMENTS

0047806  3/1982  European Pat. Off. .
  66702 12/1982  European Pat. Off. .
3041563  5/1981  Fed. Rep. of Germany .
81/03426 12/1981  PCT Int'l Appl. .

Primary Examiner—Edward M. Coven
Attorney, Agent, or Firm—Stiefel, Gross, Kurland & Pavane

[57] ABSTRACT

A blood sampling device (10), in particular intended for arterial blood sampling and blood gas analysis, is disclosed. The sampling device is provided with valve means which in the dry state permits expulsion of gas from the sampler reservoir (18), but which automatically closes on contact with blood. The valve means comprises two mating surfaces (21, 26) retained apart by an interlayer of a porous or fluffy fibrous material (22), which collapses on contact with a liquid.

15 Claims, 16 Drawing Figures

BLOOD SAMPLING DEVICE

This is a continuation of application Ser. No. 477,972, filed Mar. 23, 1983, now abandoned.

TECHNICAL FIELD

The present invention relates to a blood sampling device. In particular, the blood sampling device according to the invention is suitable for obtaining arterial blood samples for blood gas analysis.

BACKGROUND ART

The parameters determined in blood gas analysis, pH, $P_{O_2}$, and $P_{CO_2}$, are sensitive to influence from the outside environment, and thus it is necessary to take special precautions in order to avoid such influences. This need is well known in the art and patent literature relating to sampling devices for the above-mentioned purpose is comprehensive.

Different classes of sampling devices for use in connection with blood gas analysis are well known. One class of devices comprises syringes with a piston part, which under the influence of the arterial blood pressure are pushed backwards during the filling of the syringe from a starting position with the piston part fully advanced. Another class of devices comprises flattened flexible containers from which air has been expelled prior to sampling. However, a certain amount of air will remain in devices of these two classes, and precautions intended to get rid of even these traces have been disclosed.

Another type of blood sampling device for arterial blood sampling basically comprises a gas-filled sampler reservoir provided with an inlet opening as well as a venting passage to the ambient atmosphere, the venting passage having valve means cooperating therewith. Vented sampling devices of this class are well-known, e.g., from the following patent publications: published Danish patent application No. 5494/72 and corresponding U.S. Pat Nos. 3,943,917, 4,340,067, DK Nos. 2736/78, 2737/78, EP Nos. 0047806, 0047176, U.S. Pat. No. 4,299,238, DE Nos. 3018262, 3041563, U.S. Pat. Nos. 4,266,559, 4,266,558, 4,257,426, 4,206,768, 4,172,448, 4,133,304, 3,978,846, 3,960,139, 3,785,367 and WP No. 8103426.

Use of some of the well-known vented blood sampling devices requires manipulations of certain kinds in order to achieve a liquid-tight sealing of the sample reservoir. Also known are vented blood sampling devices of this type which automatically, i.e., without manipulation, permit passage of gas but not the liquid blood sample for providing a liquid-tight sealing of the venting passage. One of these devices is disclosed in the above-mentioned U.S. Pat. No. 4,340,067 and has incorporated a piece of paper material between the piston part and the walls of the sample reservoir, the paper material forming a venting means or a passageway through which air is exhausted as blood enters the chamber under arterial pressure. The passageway is automatically closed to prevent leakage from the chamber when the chamber becomes filled with blood and the paper material is wetted.

DISCLOSURE OF THE INVENTION

An improved liquid sampler or sampling device has now been devised, comprising a sample container for receiving a liquid in an inner space thereof and having a sample inlet passage and a venting passage each communicating with the inner space, a valve means comprising valve surface parts defining a sealing means for closing the venting passage, and an automatic valve actuating means for closing the valve surface parts (and hence the valve) after the sampler has been filled. In accordance with the invention, the valve surface parts are made from a liquid resistant material and at least partly define the venting passage, the surface parts being mutually movable from an open position to a closed position in which the venting passage is closed by the valve surface parts. The valve actuating means includes a liquid reacting substance disposed within the venting passage so as to be exposed to the liquid sample flowing into the passage, the valve actuating means maintaining the valve surface parts in an open position when the liquid reacting substance is in a non-wetted condition, and maintaining the valve surface parts in the closed position when the liquid reacting substance has been wetted and changed to a liquid reacted condition.

In one embodiment, the valve means of the liquid sampler comprises an elastomeric member disposed in the sample container, the valve means being operable by the expansion of the elastomeric member for closing the venting passage, and a piece of material disposed within the sample container contacting the elastomeric member, the material when dry retaining the elastomeric member in a deformed condition wherein the material is wetted by the liquid, expansion of the elastomeric member upon collapse of the material operating the valve means for closing the passage.

In a preferred embodiment, the sampling device is adapted for blood sampling and comprises a gas-filled sampler reservoir with an inlet adapted for connection to a needle, a venting passage communicating the reservoir with the ambient atmosphere, the venting passage being provided with a valve means comprising two pressurized mating or complementary surface parts having sandwiched therebetween an interlayer of a fibrous material with a fluffy or porous air-filled structure which on contact with blood and under the pressure of the mating surface collapses and thus is able to provide in cooperation with the complementary surface parts sealing of the venting passage.

The preferred blood sampling device according to the invention possesses an advantageous valve means, the sealing of which is dependent on collapse of the fibrous material and is automatically induced on contact of the porous interlayer with the liquid sample. Thereby, the closed venting passage in the blood sampling device according to the invention will be more gas tight than the closed venting passage in the blood sampling device according to U.S. Pat. No. 4,340,067.

In the present context "seal" or "sealing" means ability to maintain a closed valve function under pressure differences between the sampler reservoir and the surroundings in the order of 5000 mm Hg ($660 \times 10^3$ N/m$^2$). This figure has been estimated from the fact that arterial blood pressure in the order of 300 mm Hg should be tolerated by the valve and that even greater pressure differences may occur during introduction of the blood sample in appropriate analysis apparatus. Pressure differences in the order of 4000 mm Hg ($530 \times 10^3$ N/m$^2$) may occur in that situation and should not give rise to blood bypassing the valve.

In order to fulfill the requirements as to effective venting of air as well as effective sealing on contact with liquid, the interlayer material, the dimensions of the interlayer, and the pressure acting on the material should be adapted to each other. Suitable interlayer materials should be selected preferably from among fibrous materials such as wood fibres or textile fibres such as cellulose, cellulose acetate or viscose rayon collapsing as specified below when wetted. The dimensioning will be a matter of routine choice.

According to the invention the collapse of the porous material on which the closure of the valve function depends is such that the thickness of material subjected in wet condition to pressure of the magnitude usually found between gasket and cylinder wall in a blood sampling device and subsequently dried is equal to or less than $0.4\times$ the thickness of the untreated material, preferably equal to or less than $0.3\times$ the thickness of the untreated material and more preferably equal to or less than $0.2\times$ the thickness of the untreated material.

The venting passage communicating the sample reservoir with the ambient atmosphere and the appendant valve means may be placed at any appropriate location in the blood sampling device. Preferably, the venting passage is located in the part of the sampler reservoir remote from the inlet. An essentially total expulsion of the gas from the sampler reservoir during the filling thereof will be obtainable when using the sampling device in its usual orientation.

In a preferred embodiment of the sampling device according to the invention the sampler reservoir has a variable volume. Thus, the sampler reservoir may be formed by the syringe chamber of a syringe with a piston part or may have flexible walls and be emptied through pinching thereof. Thus, a sample may be injected directly in appropriate analysis apparatus without breakage of the seal.

In a further preferred embodiment of the blood sampling device according to the invention the pressurized mating surface parts comprise an elastomeric surface part on the piston part and an adjacent surface part on the wall of the blood sampling device. In this embodiment the interlayer of collapsible porous material may quite simply be inserted between the piston part and the wall of an ordinary blood sampling syringe.

Another preferred embodiment of the blood sampling device according to the invention has the form of a syringe provided with a piston part and further comprising a gas-filled sampler reservoir with an inlet adapted to be connected to a needle, a venting passage communicating the reservoir with the ambient atmosphere, the venting passage being provided with valve means comprising two pressurized mating or complementary surface parts, one surface part comprising a surface on an elastomeric gasket and the other surface part comprising a surface part on the piston part, the two pressurized mating or complementary surface parts having sandwiched in between an interlayer of a fibrous material with a fluffy or porous air-filled structure which on contact with blood and under the pressure of the mating surfaces will collapse.

Manufacture of variations of this embodiment may be easier automated than manufacture of the embodiment with the interlayer between the barrel wall and the piston part. This fact is of some importance in connection with the present invention which deals with devices which are to be manufactured in very large numbers at low cost.

It should be mentioned that in a blood sampling device in the form of a syringe with a piston part and a cylindrical barrel, the venting passage may suitably extend wholly or partially about the piston part, the part of the venting passage adjacent to the sampler reservoir preferably being as close to the periphery of the piston part as possible or along the periphery. Thus, an essentially total ventilation of the sampling device will be obtainable without regard to the angle between the sampling device and the horizontal. In order to ensure total or essentially total expulsion of the gas from the sampler reservoir without regard as to both axial rotation of the device and the angle between the sampling device and the horizontal, it is preferred that the part of the venting passage adjacent to the sampler reservoir have the form of an annular, possibly segmented slot between the outer periphery of the piston part and the wall of the syringe barrel.

Finally, it should be mentioned that the blood sampling device may be preloaded in a well-known manner with liquid or dry anticoagulant such as heparin in solution or in the form of crystalline or freeze-dried heparin.

Other objects, advantages and features of the present invention will become apparent from the following specification when taken in conjunction with the accompanying drawings, wherein like numerals represent like parts.

BEST MODE FOR CARRYING OUT THE INVENTION

Figure 1:
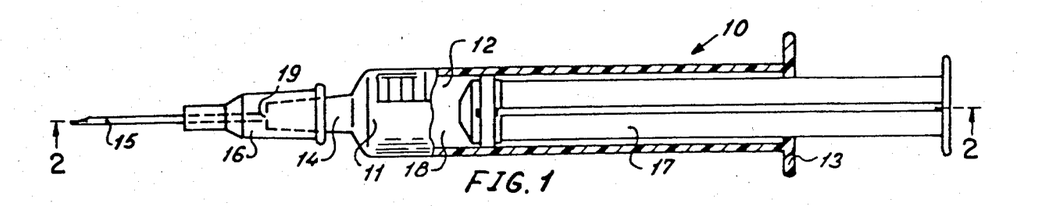
FIG. 1 is a side elevational view, partly in section, revealing the blood sampling device of the present invention in its entirety.
Figure 2:
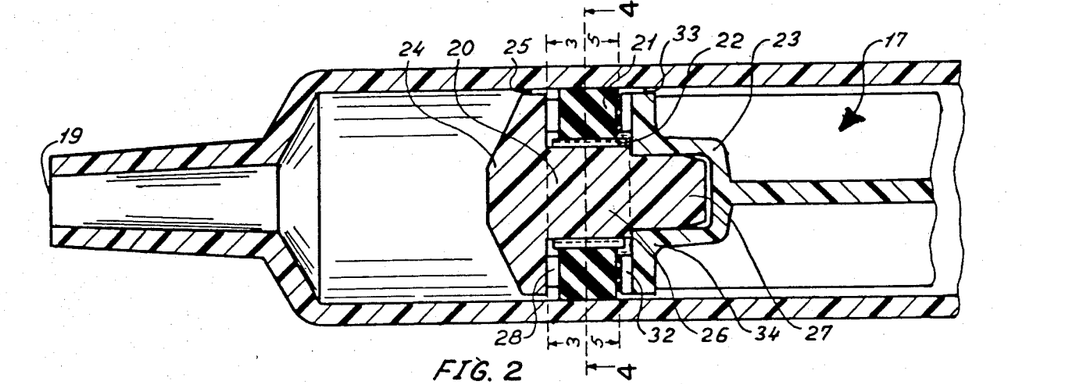
FIG. 2 is a fragmentary cross-sectional view taken substantially along line 2—2 in FIG. 1.

Referring to FIGS. 1 and 2 of the drawings the blood sampling device depicted and generally designated 10 has a relatively rigid, generally cylindrical hollow body or barrel 11 made of a suitable plastic material or glass. Such materials as well as plastic materials provided with a gas-tight coating are well known in the art. The cylindrical barrel 11 has a central bore 12 and terminates at the rear end with a finger piece 13. This finger piece 13 has the shape of an annular flange but can be any shape which provides support for the fingers. The barrel terminates at the front end in a tip 14 of generally frustoconical shape. The tip 14 is shown as carrying a hypodermic needle 15 through frictional engagement of the tapered periphery of tip 14 with the tapered end of the internal passage of a cylindrical base member 16 carrying the needle 15. A composite piston part 17 is inserted in the cylindrical barrel 11 from the rear end thereof and defines together with the barrel 11 a sampler reservoir 18. An inlet opening 19 in the tip 14 communicates the sampler reservoir 18 with the bore of the needle 15.

As shown in more detail in FIG. 2, the piston part 17 is a composite part and comprises piston elements 20, 21, 22 and 23. The piston element 20 has a generally disc-shaped front part 24 having a diameter which is slightly less than the diameter of the barrel 11, thus providing a narrow passage 25 between the wall of the barrel 11 and the front part 24.

The piston element 20 further comprises a generally cylindrical intermediate portion 26 of reduced diameter adapted for carrying the piston element 21 comprising a ring shaped elastomeric gasket and a generally cylindrical rear portion 27 of further reduced diameter adapted for carrying the piston rod 23. An interlayer 22 of a porous or fluffy, collapsible material is provided between the wall of the intermediate portion 26 and the inner wall of the ring-shaped gasket 21. The interlayer 22 is comprised of a material which exhibits greater rigidity when dry than when wet. Consequently, when the interlayer 22 is wet, it may be collapsed by application of a lower compression force than would be required to compress the interlayer when dry. The interlayer may be comprised, for example, of paper manufactured by Cleveland GP under No. 570912 or of Danish towel paper manufactured under the tradename Tapir, quality 830-80.15. The elastomeric gasket 21 and interlayer 22 are dimensioned such that when the interlayer is dry, the gasket 21 is retained in a deformed or compressed state between the interlayer 22 and barrel 11. At the same time, the frictional force between the barrel and the gasket is adeqately low to ensure relatively free movement of the piston part 17 in the barrel. A suitable material for the gasket 21 is india rubber.

Figure 3:
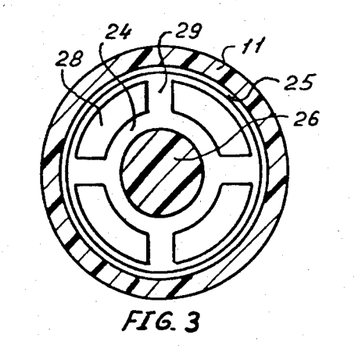
FIG. 3 is a cross-sectional view taken substantially along line 3—3 in FIG. 2 illustrating the piston and the front part of the venting passage.
Figures 4, 5:
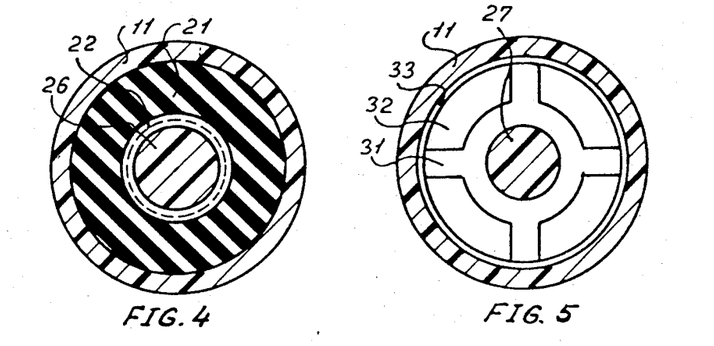
FIG. 4 is a cross-sectional view taken substantially along line 4—4 in FIG. 2 illustrating the piston and part of the venting passage comprising the venting interlayer material.
FIG. 5 is a cross-sectional view taken substantially along line 5—5 in FIG. 2 illustrating the piston and the rear part of the venting passage.

The rear side of the disc-shaped front part 24 of piston element 20 has a pattern of protruding areas as shown in more detail in FIG. 3 wherein four arcuate protrusions 28 are shown. The grooves 29 between the protrusions 28 establish fluid communication between the passage 25 and the interlayer 22, which in FIG. 4 is shown as an uninterrupted layer between the reduced diameter piston part 26 and the gasket 21. Alternatively, the interlayer could be provided as separate strips or, in another form, not covering the entire periphery of the reduced diameter portion 26. When dry the interlayer 22 has a porous air-filled or fluffy structure allowing passage of gas under pressure differentials normal to blood sampling syringes. This venting function is accomodated despite the compressive force applied on interlayer 22 by gasket 21, as long as the interlayer remains dry.

The piston rod 23 is provided with a base part 34 opposite the gasket 21. As best shown in FIG. 5, the base part 34 has on its front side a pattern of protruding areas 32 with grooves 31 very similar to the pattern on the disc-shaped front part 24. The base part 34 has a generally circular outer periphery having a diameter which is slightly less than the diameter of the barrel 11, thus providing a narrow passage 33 between the wall of the barrel 11 and the base part 34. The grooves 31 of the pattern on the front side of the base part 34 establish fluid communication between interlayer 22 and passage 33, which opens into the ambient atmosphere at the rear end of the barrel 11.

As will appear from the above, a continuous venting passage comprising passage 25, grooves 29, the porosities of the interlayer 22, grooves 31 and passage 33 establishes fluid communication between the sampler reservoir 18 and the ambient atmosphere when the sampler reservoir is unfilled or partially filled.

As the reservoir fills, blood eventually passes through passage 25, grooves 29 and into contact with the interlayer 22. Once the interlayer 22 is wet, it loses its rigidity, and collapses under the compressive force of the gasket 21. This establishes a seal of the venting passage by blocking fluid passage through the interlayer 22. At the same time, a seal is retained between the gasket 21 and barrel 11.

Figure 6:
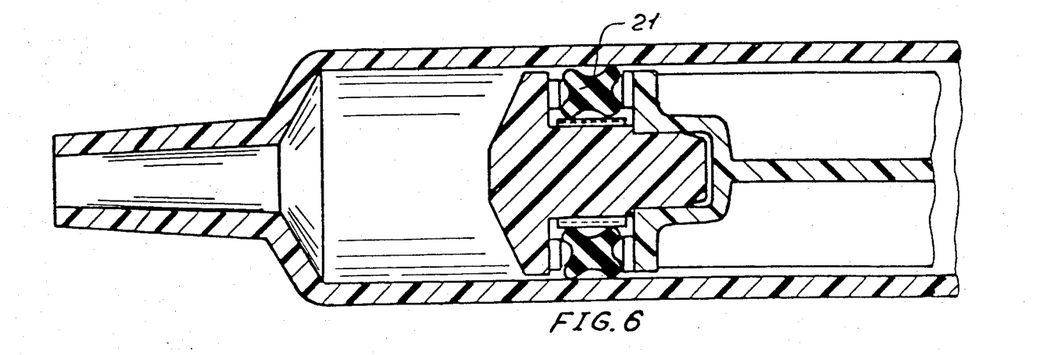
FIG. 6 is a cross-sectional view corresponding to FIG. 2 but showing an alternative shape of the elastomeric gasket of the piston part.

FIG. 6 shows a blood sampling device according to the invention which apart from the design of the gasket 21 is identical to the embodiment shown in FIGS. 1–5. The gasket design shown in FIG. 6 has the advantage of providing within a given tolerance range a smaller variation in the force acting against the barrel wall and also a greater contact pressure by virtue of the reduced contact area.

Figure 7:
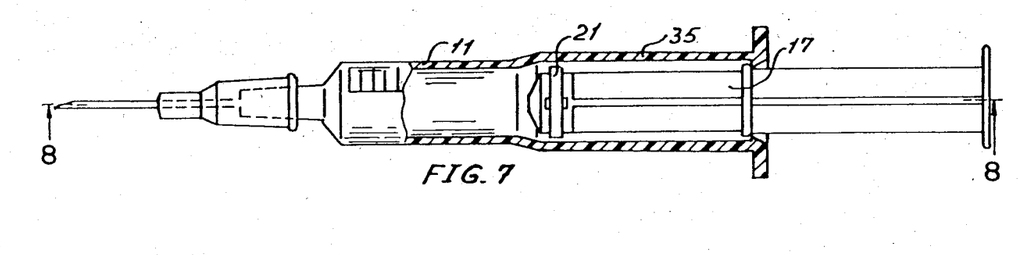
FIG. 7 is a side elevational view corresponding to FIG. 1 but showing an alternative syringe barrel suited for long-term storage.
Figure 8:
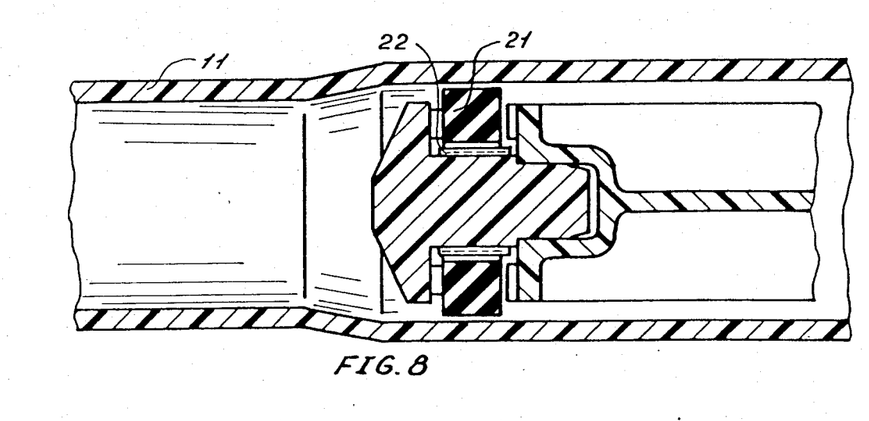
FIG. 8 is a fragmentary cross-sectional view taken substantially along line 8—8 in FIG. 7.

In view of the shelf storage time anticipated in connection with blood sampling devices according to the present invention, a preferred embodiment having a specially designed barrel is shown in FIGS. 7 and 8. The rear end of the barrel 11 has an enlarged diameter portion 35 wherein the piston part 17 is located during storage in a retracted, unstressed position (FIG. 8). Just before use the piston part is advanced to the reduced diameter portion of the barrel, thus establishing the necessary seal between the gasket 21 and the barrel wall.

When drawing an arterial blood sample by normal use of the blood sampling devices according to FIGS. 1–8, the barrel 11 is held firmly in one hand and using the other hand the piston part 17 is set to a position where the volume of the sampler reservoir 18 is equivalent to the volume of the blood sample to be drawn. A hollow hypodermic needle 15 of the usual type is then mounted on the tip 14 of the blood sampling device and the bevelled end of the needle is thereafter introduced into an artery. On penetration of the arterial wall the arterial blood pressure will force blood to flow through the needle and into the blood sampling device. As the sampler reservoir fills with arterial blood the gas present in the sampler reservoir will be displaced and escape through the venting passage to the ambient atmosphere.

When the blood level reaches and wets the interlayer 22, the material will lose its rigidity and collapse as the adjacent gasket material expands thereby sealing the venting passage for preventing the passage of blood to the back-side of the piston and accordingly reducing the risk of contamination arising from blood leakage. At the same time the sample will be effectively protected against contamination with atmospheric air and accordingly the risk of achieving erroneous measurement results in a subsequent blood gas analysis will be reduced. It will be apparent from the foregoing that the sealing of the venting passage is automatically induced by the contact between the collapsible interlayer and the liquid blood sample.

Subsequent to filling, the blood sampling device is withdrawn from the sampling location and after removal of the needle the sample may be introduced directly into appropriate analytical instrumentation.

Further embodiments of the blood sampling device according to the invention and details thereof are shown in FIGS. 9–16. The embodiments are very similar to each other, only the position of the collapsible interlayer and the orientation of the venting passage being different.

Referring now to FIGS. 9–13, these figures illustrate an embodiment of the blood sampling device in which the collapsible material 122 is disc-shaped as compared to the embodiment of FIGS. 1–8 in which a tubular shape is used. The alternative selected is a matter of choice mainly dependent on the ease of assemblage.

Figure 9:
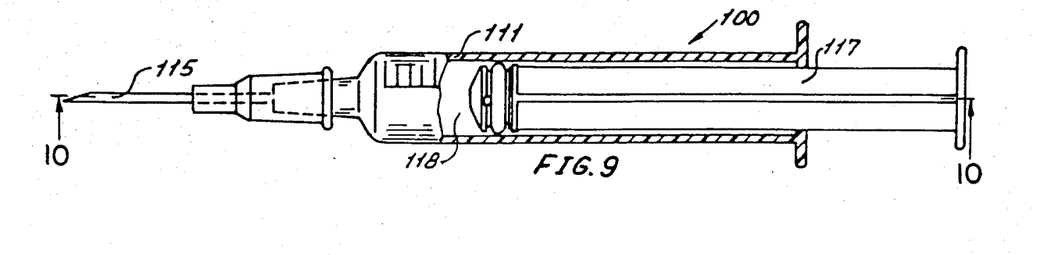
FIG. 9 is a side elevational view corresponding to FIG. 1 but showing yet a further alternative embodiment of the blood sampling device of the invention.
Figure 10:
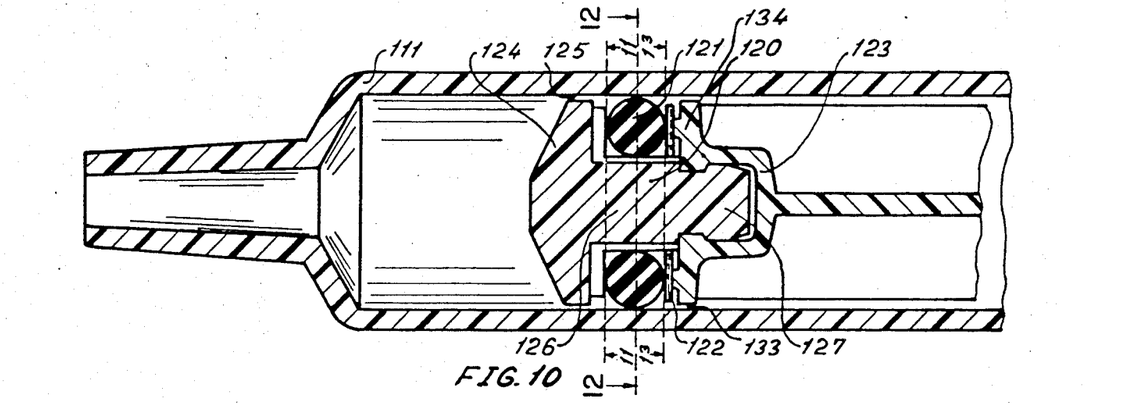
FIG. 10 is a fragmentary cross-sectional view taken substantially along line 10—10 in FIG. 9.

The blood sampling device shown in FIGS. 9 and 10 and generally designated as 100 comprises, like the previously described blood sampling devices, a barrel 111 adapted to carry a needle part 115 and a composite piston part 117 which together with the barrel 111 defines a sampler reservoir 118. The composite piston part 117 comprises piston elements 120, 121, 122, 123. The piston element 120 has a generally disc-shaped front part 124 with a diameter which is slightly less than the diameter of the barrel 111, thus providing a narrow passage 125 between the wall of the barrel 111 and the front part 124.

Figure 11:
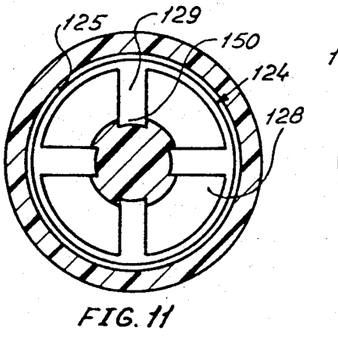
FIG. 11 is a cross-sectional view taken substantially along line 11—11 in FIG. 10 illustrating the piston and the front part of the venting passage.
Figure 12:
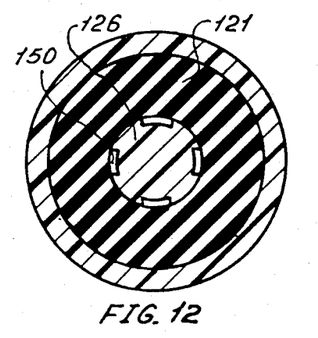
FIG. 12 is a cross-sectional view taken substantially along line 12—12 in FIG. 10 illustrating the piston and the intermediate part of the venting passage.
Figure 13:
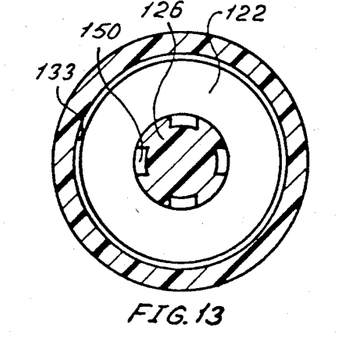
FIG. 13 is a cross-sectional view taken substantially along line 13—13 in FIG. 10 illustrating the piston and the rear part of the venting passage.

The piston element 120 further comprises a generally cylindrical intermediate portion 126 of reduced diameter provided with axial grooves 150 and adapted for carrying the ring-shaped gasket 121. The piston element 120 also comprises a generally cylindrical rear portion 127 of further reduced diameter adapted for carrying the piston rod 123. A disc-shaped interlayer 122 of a porous or fluffy, collapsible material is provided between the O-ring gasket 121 and a base part 134 of the piston rod 123. The O-ring gasket 121 is of a type fulfilling the requirements set forth above in connection with gasket 21 best shown in FIG. 2. The rear side of the disc-shaped front part 124 of piston element 120 has a pattern of protruding areas as shown in more detail in FIG. 11 showing a pattern of four arcuate protrusions 128. The grooves 129 and protrusions 128 establish fluid communication between the passage 125 and the axial grooves 150 in the intermediate portion 126.

The base part 134 of the piston rod 123 has a generally circular outer periphery with a diameter slightly less than the diameter of the barrel 111, thus providing a narrow passage 133 between the wall of the barrel 111 and the base part 134. Thus, the porous interlayer 122 provides fluid communication between the axial grooves 150 and the passage 133 which opens into the ambient atmosphere.

As will appear from the above, a continuous venting passage comprising passage 125, grooves 129, grooves 150, the porosities of interlayer 122 and passage 133 establishes fluid communication between the sampler reservoir 118 and the ambient atmosphere in the unfilled or partially filled blood sampling device 100.

When the blood sampling device 100 is completely filled, a liquid as well as gas-tight seal is established in the region of the interlayer 122 by the mechanism previously described.

Figure 14:
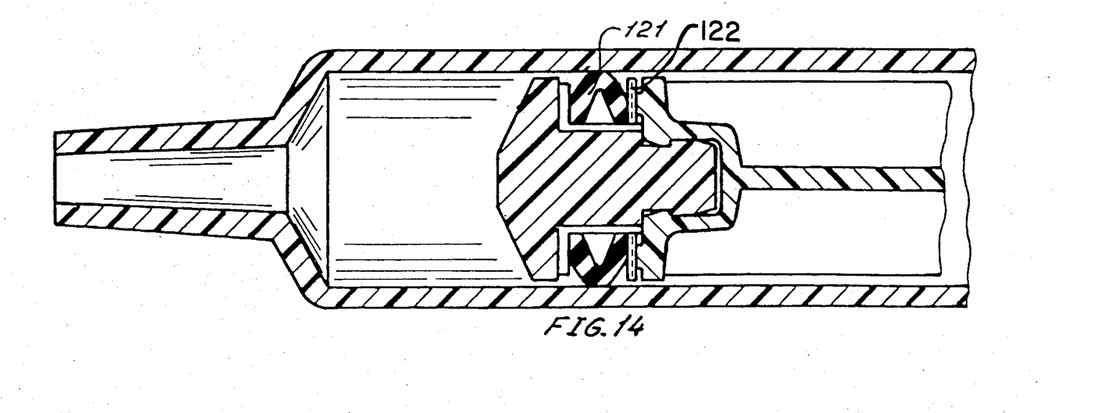
FIG. 14 is a cross-sectional view corresponding to FIG. 10 but showing an alternative shape of the elastomeric gasket of the piston part.

FIG. 14 shows a blood sampling device according to the invention which apart from the design of the gasket 121 is identical with the embodiment shown in FIGS. 9–13. The gasket design shown in FIG. 14 has the advantage of providing a relatively large pressure on the interlayer 122 for a given pressure of the gasket against the cylinder wall.

Figure 15:
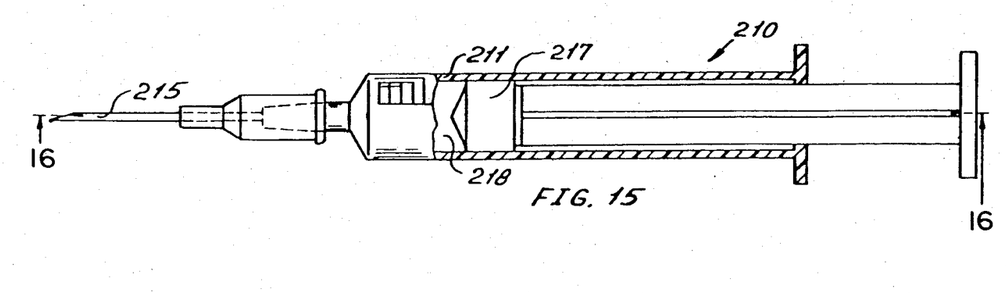
FIG. 15 is a side elevational view corresponding to FIG. 1 and showing still another embodiment of the blood sampling device of the invention.
Figure 16:
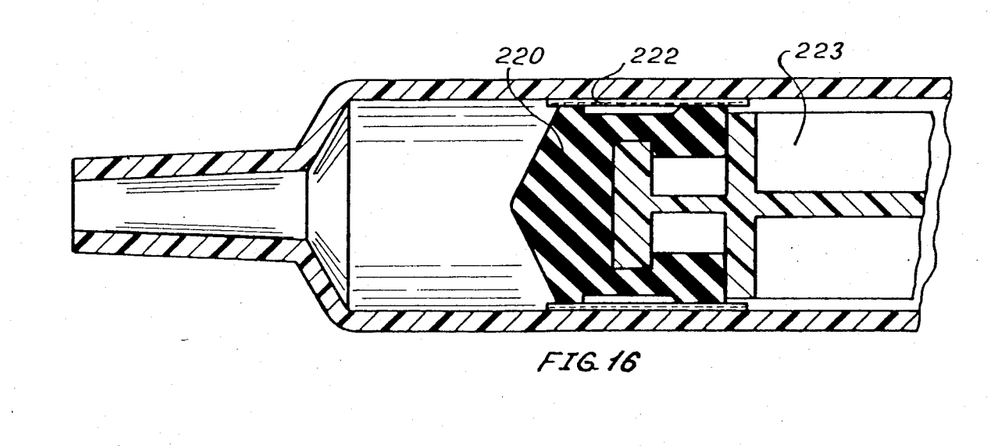
FIG. 16 is a fragmentary cross-sectional view taken substantially along line 16—16 in FIG. 15.

FIGS. 15 and 16 show a further embodiment 210 of a blood sampling device according to the invention. Again, a cylindrical barrel 211 is adapted to carry a needle part 215 and a composite piston part 217 which together with the barrel 211 defines a sampler reservoir 218. The composite piston part 217 comprises piston elements 220, 222, 223.

Piston element 220 is made from an elastomeric material and is adapted to fit into the cylinder barrel in the manner set forth above in connection with the gasket 21. Wrapped around the piston element 220 is a thin layer 222 of a porous or fluffy material of the type described above in connection with interlayer 22. Thus, layer 222 is sandwiched between the piston element 220 and the wall of the barrel 211. Layer 222 may also be in the form of separate axially extending strips and may extend over the whole surface of piston element 220 or only part thereof. As will now be apparent, a venting passage extending from the sampler reservoir 218 to the ambient atmosphere is provided by the porosities of interlayer 222, the said venting passage being sealed automatically on contact with the liquid sample.

It should be understood that the present invention is not limited to the particular construction and arrangement of parts disclosed and illustrated herein, but embraces all modified forms thereof that fall within the scope of the following claims.

What is claimed is:

1. A liquid sample comprising: a sample container for receiving a liquid sample in an inner space thereof and having a sample inlet passage and a venting passage each communicating with the inner space; valve means comprising valve surface parts, said surface parts being made from a liquid resistant material and at least partly defining said venting passage, said surface parts being mutually movable from an open position to a closed position in which the venting passage is closed by said valve surface parts and a liquid reacting substance so disposed within the venting passage that it is exposed to the liquid sample flowing into the venting passage, said liquid reacting substance maintaining the valve surface parts in their open position when the liquid reacting substance is in a non-wetted condition and permitting the valve surface parts to move into their closed position when the liquid reacting substance is wetted by the liquid sample.

2. A liquid sampler according to claim 1, wherein the sample container is in the form of a syringe cylinder having a piston movably arranged therein.

3. A liquid sampler comprising a sample container, and valve means, wherein said sample container receives a liquid sample in an inner space thereof and has a sample inlet passage and a venting passage each communicating with the inner space of the sample container, said valve means comprising valve surface parts and a liquid reacting substance, said valve surface parts defining a sealing means for closing said venting passage, said surface parts being made from a liquid resistant material and being movable from an open position to a closed position, and being normally biased toward the closed position, said liquid reacting substance being disposed at a location within the venting passage so as to be exposed to the liquid sample flowing into the venting passage, the liquid reacting substance having sufficient rigidity in its non-wetted condition to maintain the valve surface parts in said open position and insufficient rigidity in its wetted condition to maintain the valve surface parts in said open position, and said valve means maintaining the valve surface parts in said closed position when the liquid reacting substance has been exposed to the liquid sample and is in a wetted condition.

4. A liquid sampler according to claim 3, wherein the liquid reacting substance is an interlayer of a material with a porous air-filled structure sandwiched between said valve surface parts, and wherein one of said valve surface parts is an elastomeric member exerting a compressive force on the liquid reacting substance sufficient to place the valve surface parts in said closed position when the liquid reacting substance is in a wetted condition.

5. A liquid sampler according to claim 4, and further comprising means for varying the volume of the sample container.

6. A liquid sampler according to claim 5, wherein the liquid sampler is a syringe and the volume varying means comprises a piston.

7. A liquid sampler according to claim 6, for sampling blood, wherein said elastomeric member comprises an elastomeric surface on said piston, wherein said liquid reacting substance is gas permeable when dry and is disposed between said elastomeric surface and the inner wall of the syringe, and wherein said valve means comprises said elastomeric surface, said liquid reacting substance and said inner wall, a seal being established between said surface and said inner wall upon collapse of said liquid reacting substance.

8. A liquid sampler according to claim 7, wherein said liquid reacting substance is secured to said elastomeric piston surface for movement with said piston.

9. A liquid sampler according to claim 8, wherein said piston includes a main part and an elastomeric gasket disposed on said main part, said elastomeric surface comprising a surface of said gasket.

10. A liquid sampler according to claim 9, wherein said liquid reacting substance is a fibrous material.

11. A liquid sampler according to claim 10, wherein said fibrous material is a cellulosic material.

12. The liquid sampler according to claim 6, wherein said piston includes a main part and an elastomeric gasket on said main part, said elastomeric surface comprising a surface of said gasket, wherein said liquid reacting substance is gas permeable when dry and is disposed between said elastomeric gasket and a surface of said main part, and wherein said valve means comprises said elastomeric surface, said liquid reacting substance and said main part, a seal being established between said elastomeric surface and said main part upon collapse of said liquid reacting substance.

13. A liquid sampler according to claim 12, wherein said liquid reacting substance is secured to said elastomeric piston surface for movement with said piston.

14. A liquid sampler according to claim 13, wherein said liquid reacting substance is a fibrous material.

15. A liquid sampler according to claim 14, wherein said fibrous material is a cellulosic material.

* * * * *

UNITED STATES PATENT AND TRADEMARK OFFICE
CERTIFICATE OF CORRECTION

PATENT NO. : 4,657,028

DATED : April 14, 1987

INVENTOR(S) : Russell Rich et al.

It is certified that error appears in the above—identified patent and that said Letters Patent is hereby corrected as shown below:

Title page, item [56] under "FOREIGN PATENT DOCUMENTS", insert
--0047176 European Pat. Off.
3018262 Fed. Rep. of Germany--

Column 2, after line 28, insert the following:
--venting passage is opened, the material being collapsible by the force exerted by the elastomeric member when the--

Signed and Sealed this

Fifth Day of April, 1988

*Attest:*

DONALD J. QUIGG

*Attesting Officer*     *Commissioner of Patents and Trademarks*